USO05474782A

United States Patent [19]
Winter et al.

[11] Patent Number: 5,474,782
[45] Date of Patent: Dec. 12, 1995

[54] WOUND-HEALING COMPOSITION AND METHOD

[75] Inventors: Rudolph E. K. Winter; Stephen A. Kolodziej; Walter H. Lewis, all of St. Louis, Mo.

[73] Assignee: WoundFast Pharmaceuticals, Inc., St. Louis, Mo.

[21] Appl. No.: 246,631

[22] Filed: May 20, 1994

[51] Int. Cl.$^6$ ..................................................... A61K 9/70
[52] U.S. Cl. ............................................ 424/443; 514/559
[58] Field of Search .................... 424/443, 445; 514/559

[56] References Cited

U.S. PATENT DOCUMENTS

| | | | |
|---|---|---|---|
| 3,694,557 | 9/1972 | Persinos | 424/279 |
| 4,120,964 | 10/1978 | Hartenstein et al. | 424/258 |
| 4,183,939 | 1/1980 | Gieske et al. | 424/258 |
| 4,597,961 | 7/1986 | Etscorn | 424/28 |
| 4,782,077 | 11/1988 | de la Parra | 514/423 |
| 4,844,901 | 7/1989 | Keplinger et al. | 424/195.1 |
| 5,069,904 | 12/1991 | Masterson | 424/401 |
| 5,156,847 | 10/1992 | Lewis et al. | 424/447 |

OTHER PUBLICATIONS

Lewis, W. H., et al., "Introduction to the Ethnobotanical Pharmacopeia of the . . . ", Medicinal and Poisonous Plants of the Tropics, The Netherlands (1987).
Vaisberg et al., "Taspine is the Cicatrizant Principle . . . ", Planta Medica 55 (1989).
Southan and Buckingham, Dictionary of Alkaloids, Chapman and Hall, London and New York, summary from pp. xxiv–xxv (1989).
Persinos Purdue et al., South American Plants II: Taspine Isolation and Anti–Inflammatory Activity, Journal of Pharmaceutical Sciences, vol. 68, No. 1, (Jan., 1979).
Webster's Third New International Dictionary, Ed. P. B. Gove, Merriam–Webster, Inc., Springfield, Massachusetts, pp. 108, 1707 & 2406, (1986).
Morrison and Boyd, Organic Chemistry, third edition, Allyn and Bacon, Inc. Boston, pp. 30–32 (1973).
Platanova, T. F., et al., "Study of Plant Alkaloids," *Leontice ewersmannii*, BGE, IV. Structure of the Alkaloid Taspine [1], pp. 2957–2961 (1956) (*J. of General Chemistry U.S.S.R.* 23: 921–926 (1953)).
Ross, Russell, "The Fibroblast and Wound Repair," *Biol. Rev.* 43, pp. 51–96 (1986).
Peacock, Jr., *Wound Repair,* Ch. 5, "Collagenolysis and The Biochemistry of Wound Healing," 3d Ed., pp. 102–140, W. B. Saunders, Philadelphia (1984).
Mustoe, Thomas., et al., "Accelerated Healing of Incisional Wounds in Rats Induced by Transforming Growth Factor–β," *Science* 237: 1333–1335 (1987).
Porras–Reyes, Beatriz H., et al., "Enhancement of Wound Healing by the Alkaloid Taspine Defining Mechanism of Action," *Proc. of the Soc. for Experimental Biology and Medicine* 203: 18–25 (1993).

Primary Examiner—Thurman K. Page
Assistant Examiner—Sharon Howard
Attorney, Agent, or Firm—Rothwell, Figg, Ernst & Kurz

[57] ABSTRACT

A wound-healing composition and method utilizing a compound of the Formula (I)

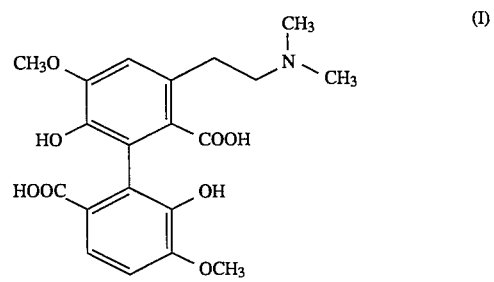

or a pharmaceutically acceptable salt thereof.

30 Claims, 1 Drawing Sheet

WOUND-HEALING COMPOSITION AND METHOD

BACKGROUND OF THE INVENTION

1. Field of the Invention

The present invention relates to compositions and methods useful for healing of wounds and the like.

2. Description of the Background Art

There is continuing medical interest in materials and methods which promote and accelerate the healing of wounds.

Wound-healing strength can be measured in newtons (N) or expressed in $g/mm^2$ ($\times 1000/9.8$) (Tensometer 10, Monsanto Co., St. Louis, Mo., U.S.A.) utilizing a linear skin incision model in rats, as is well documented (Ross, "The Fibroblast and wound repair," *Biological Review* 43: 51–96 (1968); Peacock Jr., "Wound Repair," ed. 3. W. B. Saunders, Philadelphia (1984); Mustoe et al., "Accelerated healing of incisional wounds in rats induced by transforming growth factor-B," *Science* 237: 1333–1335 (1987). This technique is a recognized model in assessing the generation of wound strength, the most important aspect of wound-healing (Mustoe et al., supra).

As described in U.S. Pat. No. 5,156,847 issued Oct. 20, 1992 to Lewis et al. and in Porras-Reyes et al., *Proc. Soc. Exp. Bio. Med.* 203: 18–25 (1993), a wound-healing composition of the aporphine-derived alkaloid taspine, dissolved in non-aqueous solvent, such as dimethylsulfoxide (DMSO), was shown to promote wound healing. However, taspine is practically insoluble in most conventional vehicles, including water, alcohol, saline solutions, and the like.

There remains a need in the art for new compositions and methods which can be effectively, safely, and economically administered and utilized to accelerate the healing rate of wounds, and which preferably are soluble in aqueous media.

SUMMARY OF THE INVENTION

In accordance with the present invention, a wound-healing composition comprises a pharmaceutically acceptable salt of a compound of the Formula (I)

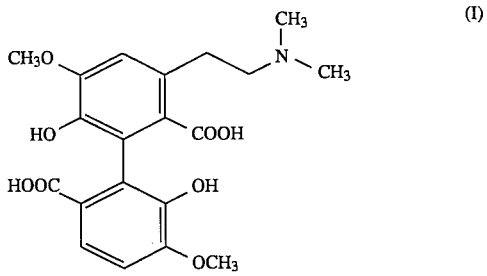

Also disclosed are wound dressings and methods of treating wounds utilizing a compound of the Formula (I), or pharmaceutically acceptable salts thereof.

DETAILED DESCRIPTION OF THE PREFERRED EMBODIMENTS

Figure 1:
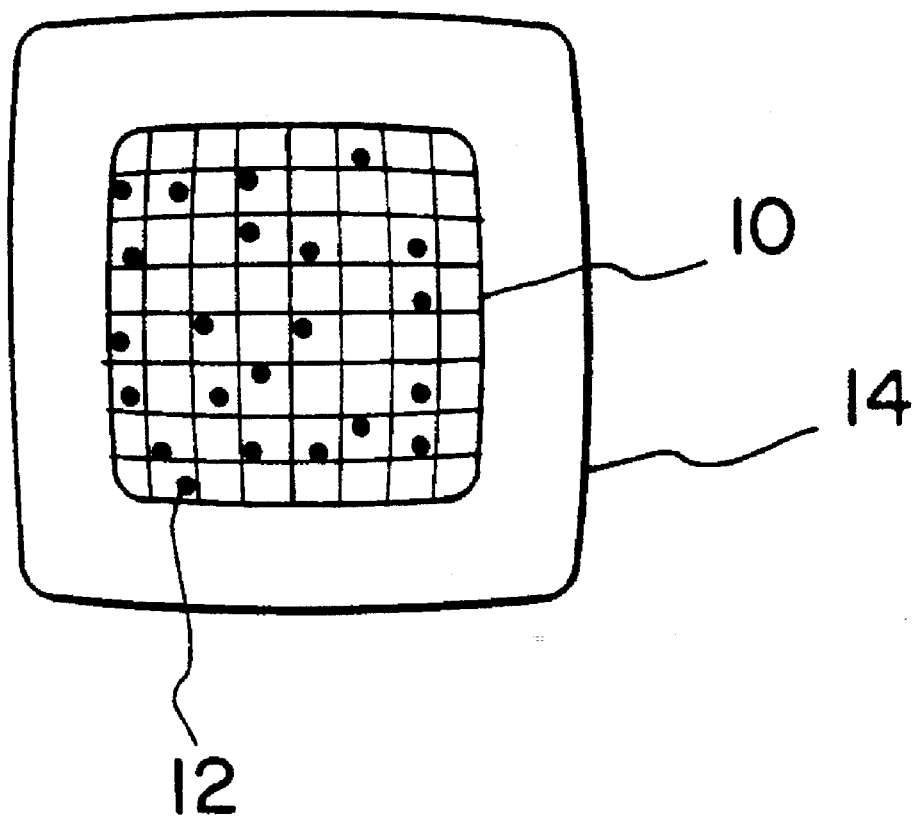
FIG. 1 is an elevational view, partly schematic, of a pre-packaged wound dressing with a sterile bandage including the wound-healing compound of Formula (I) or its salt, in accordance with one embodiment of the present invention.

Accordingly to one aspect, the present invention is applicable to a pharmaceutically acceptable salt of a compound of the Formula (I), supra, including all tautomeric forms of the pharmaceutically acceptable salts.

The term "pharmaceutically acceptable salts" may include salt-forming cations selected from the group consisting of cations of alkali metals, alkaline earth metals, copper, zinc, manganese, nickel, ammonia and organic ammonium.

The term "alkali metals" includes lithium, sodium, potassium, cesium and rubidium; and the term "alkaline earth metals" includes beryllium, magnesium, calcium, strontium and barium.

The term "organic ammonium" includes those prepared from low molecular weight organic amines, i.e., having a molecular weight below about 300, and such organic amines include alkyl amines, alkylene amines and alkanol amines, which in preferred embodiments, include two or fewer amine groups, such as methylamine, ethylamine, n-propylamine, isopropylamine, propylenediamine, primary aryl amines, such as aniline, methoxyaniline, ethoxyaniline, o,m, p-toluidine, phenylenediamine, 2,4,6-tribromoaniline, benzidine, naphthylamine, o,m,p-chloroaniline and the like, and heterocyclic amines such as pyridine, morpholine, piperidine, pyrrolidine, indoline, azepine and the like.

In preferred embodiments, the wound-healing compound of the invention is present as a sodium salt thereof.

In particularly preferred embodiments of the present invention, the inventive wound-healing compound or its salt is present in a pharmaceutically acceptable carrier, most preferably an aqueous carrier such as sterile, deionized water, saline solution (e.g., 0.9% NaCl), pharmaceutically acceptable buffer solutions, and the like.

A particularly preferred physiologically acceptable or tolerable liquid carrier is standard saline (0.9% saline solution). The levels of significance of wound healing using saline solutions at various concentrations of a monosodium salt of the compound of Formula (I) have been up to $P=<0.002$. Furthermore, no effects have been found, either irritating and hence negative, or healing and thus positive, of the saline solution alone when compared to controls.

Compositions in accordance with the present invention can include the inventive compound or its salt in a liquid carrier at wound-healing concentrations expressed in terms of equivalents of taspine, described in U.S. Pat. No. 5,156,847, incorporated herein by reference. Such wound-healing concentrations of the inventive compound or salts thereof include about 0.05–5 mg/mL, more preferably about 0.1–1 mg/mL and most preferably about 0.2–0.5 mg/mL, all concentrations referenced to standard solutions. Alternatively, the inventive compound or salt can be present in a form, such as a cream, salve, foam, lotion, collagen preparation, gel, ointment and the linear, for example, the above-noted concentrations.

The inventive compound or salt can be applied to a wound in a pharmaceutically acceptable liquid carrier such as standard saline, wherein the compound is at a concentration of from about 200 μg/mL to about 500 μg/mL, expressed in terms of taspine equivalents.

Advantageously, the inventive compositions are in pharmaceutical dosage unit form.

The present invention is also applicable to a wound dressing, and preparation thereof. In accordance with this aspect of the invention, a wound dressing is provided which includes a sterile bandage 10 onto which a compound or salt 12 in accordance with the invention has been deposited or applied. The inventive compound or salt can be applied by contacting a bandage material with an aqueous solution, other solvent or mixture containing the inventive compound or salt, and thereafter evaporating the solution from the bandage, resulting in a dried bandage 10 containing the wound healing compound or salt 12. Alternately, the inventive compound or salt can be applied to a bandage surface which has been moistened using glycerine or similar substances on the surface, or mixed with such substances and applied to the bandage surface. The thus prepared bandage, either dry or moist, can be provided sealed within a package 14.

In a method of treating wounds in accordance with the present invention, a wound-healing-effective amount of a compound or composition in accordance with the present invention, or a pharmaceutically acceptable salt thereof, is applied to a wound. In preferred embodiments, the inventive compound or salt is applied to the wound so as to provide the wound with about 0.05–5 mg/cm$^2$ thereof, more preferably about 0.1–0.5 mg/cm$^2$ and most preferably about 0.2–0.4 mg/cm$^2$, expressed in terms of taspine equivalents.

Advantageously, the inventive compound or salt is applied to a wound site after cleansing thereof, either as a single dose, or as a plurality of administrations over a period of time during healing. In preferred embodiments, the inventive compound or salt is applied at least once or twice a day for up to seven or more days after wounding or initiation of treatment.

The invention is illustrated by the following examples, which are not intended to be limiting.

EXAMPLE I

Preparation of Wound-Healing Compounds and Salts

A. Isolation of Taspine

Lyophilized sap of Croton lechleri (Euphorbiaceae) was mixed with deionized water and 1N aqueous HCl added to bring the pH to 2.0. The resulting red-brown slurry was stirred at room temperature for 24 hours. Thereafter, the mixture was neutralized with 1N aqueous NaOH and additional alkali was used to adjust to pH 8.5. Following basification, the mixture was extracted exhaustively with chloroform using a continuous extractor, the chloroform extract was dried over anhydrous sodium sulfate, and the solvent removed under reduced pressure. A light brown solid residue was obtained. Recrystallization from methanol furnished purified taspine as a light tan to white solid.

B. Taspininic Acid

A mixture of purified taspine in millipore-filtered deionized water containing 2 equivalents of NaOH was stirred at room temperature for 2.5 hours. After heating to 80° C. for an additional 0.5 hour, a clear solution of disodium taspininate (taspininic acid disodium salt) was obtained. Acidification of this solution with aqueous HCl to pH 3.5 gave taspininic acid (Platonova et al., supra).

C. Sodium Salt of Formula (I)

After cooling of the disodium taspininate solution, 1N HCl was added portionwise until a first faint cloudiness appeared. Normal NaOH was added to adjust the pH to 7.5, and the light orange solution was rendered colorless by treatment with neutral Norite. Additional millipore-filtered deionized water to adjust the total volume and filtration through a 5μ millipore filter provided the monosodium salt of the compound of Formula (I), shown in one tarotomeric form as Formula (II) below.

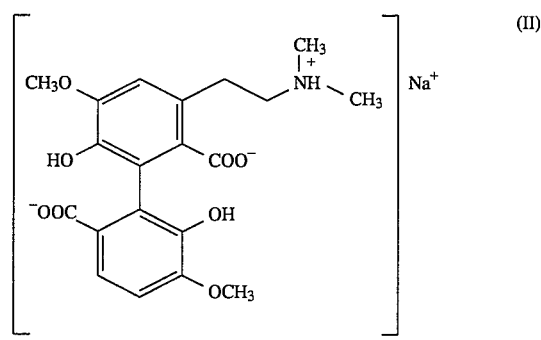

EXAMPLE II

Wound-Healing using the salt of Formula (II) in Saline

Solutions of the monosodium salt shown in Formula (II) (hereinafter sometimes referred to as "experimental" salt) in standard saline (0.9% NaCl) at concentrations of 100 μg/mL, 200 μg/mL, and 300 μg/mL taspine-equivalents were tested on rat wounds against standard saline alone. These tests were conducted under blind conditions. After wounds were coapted with surgical clips, control and experimental solutions were first administered to respective wound sites by syringe. Results and their statistical analyses using the paired T test were based on a minimum of four rats in each grouping.

The tensile strength of wounds 5 and/or 7 days after administration at concentrations of 100 μg/mL, 200 μg/mL, and 300 μg/mL taspine equivalents of the experimental salt solutions compared to a saline solution alone (control) is shown in Table 1. Results show significant levels of wound-healing by the experimental salt at concentrations of 300 μg/mL when data 5 and 7 days after wounding are pooled, but there was no significant difference between the experimental salt solutions and controls at concentrations of 100 μg/mL and also 200 μg/mL when pooled. As a whole (100–200–300 μg/mL doses), 5 day old wounds did not heal significantly faster between experimental salt-treated and control-treated incisions, whereas 7 day old wounds which included only 200 and 300 μg/mL concentrations proved significantly different between experimental- and control-treated wounds. When each group of rats was analyzed separately, those after 5 days using 100 μg/mL and 200 μg/mL were not different, but significantly greater healing was obtained using experimental-treated wounds after 7 days for both 200 μg/mL and 300 μg/mL concentrations. Further, those wounds at 5 days following treatment with 300 μg/mL of the experimental salt also showed significantly increased wound-healing compared to controls.

TABLE 1

| Dose (μg/mL) | Days | No. rats | Tensometric readings | | P = |
|---|---|---|---|---|---|
| | | | Formula (II) | Control | |
| 100 | 5 | 6 | 2.57 ± 0.30 | 2.67 ± 0.28 | NS |
| 200 | 5 & 7 | 16 | 2.77 ± 0.29 | 2.37 ± 0.23 | NS |
| 300 | 5 & 7 | 12 | 2.25 ± 0.51 | 1.82 ± 0.46 | <0.002 |
| 100–300 | 5 | 22 | 2.26 ± 0.25 | 2.17 ± 0.28 | NS |

TABLE 1-continued

| Dose (μg/mL) | Days | No. rats | Tensometric readings Formula (II) | Control | P = |
|---|---|---|---|---|---|
| 200–300 | 7 | 12 | 3.11 ± 0.43 | 2.33 ± 0.36 | 0.003 |
| 200 | 5 | 12 | 2.63 ± 0.31 | 2.54 ± 0.20 | NS |
| 200 | 7 | 4 | 3.20 ± 0.64 | 1.86 ± 0.23 | 0.05 |
| 300 | 5 | 4 | 0.66 ± 0.06 | 0.31 ± 0.06 | <0.04 |
| 300 | 7 | 8 | 3.07 ± 0.59 | 2.57 ± 0.31 | <0.02 |

Tensometric readings using Formula (II) salt and controls in rats at 5 and/or 7 days following administration of 100 μg/mL, 200 μg/mL, and 300 μg/mL. Rat tensile strength readings (N) = M ± SEM.

These data were confirmed by percent increases of wound-healing using the experimental salt in saline when compared to controls. At 100 μg/mL after 5 days there was no increase in healing, and healing was also minimal (3.5%) using 200 μ/mL after 5 days, which, however, when pooled with 7 day old data provided a 37.8% increase in wound-healing compared to control. Further, at a concentration of 300 μg/mL, acceleration of wound-healing at 5 and 7 days after incision reached an average of 66.3%.

EXAMPLE III

Administration in about 60% of rats of second doses of the experimental salt solutions two days following initial treatment showed no significant differences in pooled results in which one or two applications were administered when compared to saline controls (Table 2). However, when concentrations only of 200–300 μg/mL taspine-equivalents of the experimental salt were administered twice and healing occurred for 7 days, wound-healing using the experimental salt was much more rapid when compared with saline controls, a highly significant (P=<0.003) 74.9% increase.

TABLE 2

| No. Applications | No. rats | Dose (μg/mL) | Day | Tensometric Readings Formula (II) | Control | P = |
|---|---|---|---|---|---|---|
| 1 | 13 | 100–300 | 5 | 2.29 ± 0.40 | 2.08 ± 0.37 | NS |
| 2 | 21 | 100–300 | 5 & 7 | 2.72 ± 0.27 | 2.32 ± 0.24 | NS |
| 2 | 9 | 100–200 | 5 | 2.20 ± 0.20 | 2.30 ± 0.31 | NS |
| 2 | 12 | 200–300 | 7 | 3.11 ± 0.43 | 2.33 ± 0.36 | <0.003 |

Tensometric readings using one or two applications of the Formula (II) salt and saline control in rats at 5 and/or 7 days. Tensile strength readings (N) = M ± SEM.

What is claimed is:

1. A wound-treating composition comprising a pharmaceutically acceptable salt of a compound of the Formula (I)

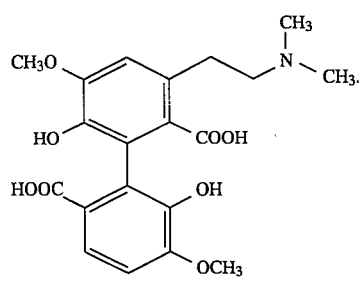

2. The composition of claim 1, wherein said salt includes a salt-forming cation selected from the group consisting of cations of alkali metals, alkaline earth metals, copper, zinc, manganese, nickel, ammonium and organic ammonium.

3. The composition of claim 1, wherein said salt is a monosodium salt.

4. The composition of claim 1, including a pharmaceutically acceptable carrier.

5. The composition of claim 4, wherein said salt is a monosodium salt.

6. The composition of claim 4, wherein said pharmaceutically acceptable carrier is an aqueous carrier.

7. The composition of claim 6, wherein said pharmaceutically acceptable salt is a monosodium salt.

8. The composition of claim 6, wherein said compound is present in said aqueous carrier at a concentration of about 0.05–5 mg/mL.

9. The composition of claim 8, wherein said salt is a monosodium salt.

10. The composition of claim 8, wherein said concentration is about 0.1–1 mg/mL.

11. The composition of claim 10, wherein said salt is a monosodium salt.

12. The composition of claim 10, wherein said concentration is about 0.2–0.5 mg/mL.

13. The composition of claim 12, wherein said salt is a monosodium salt.

14. The composition of claim 4, wherein said pharmaceutically acceptable carrier comprises a member selected from the group consisting of cream, salve, foam, lotion, collagen preparation, gel and ointment.

15. A method of treating a wound comprising application to said wound a wound-healing-effective amount of a compound of the Formula (I)

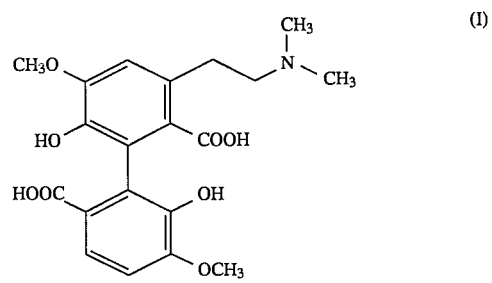

or a pharmaceutically acceptable salt thereof.

16. The method of claim 15, wherein said salt includes a salt-forming cation selected from the group consisting of cations of alkali metals, alkaline earth metals, copper, zinc, manganese, nickel, ammonium and organic ammonium.

17. The method of claim 15, wherein said salt is a monosodium salt.

18. The method of claim 15, wherein said compound is applied to said wound so as to provide said wound with about 0.05–5.0 mg/cm$^2$ of said compound or a pharmaceutically acceptable salt thereof.

19. The method of claim 18, wherein said salt is a monosodium salt.

20. The method of claim 18, wherein about 0.1–0.5 mg/cm$^2$ of said compound or a pharmaceutically acceptable salt thereof is applied to said wound.

21. The method of claim 20, wherein said salt is a monosodium salt.

22. The method of claim 18, wherein about 0.2–0.4 mg/cm$^2$ of said compound or a pharmaceutically acceptable salt thereof is applied to said wound.

23. The method of claim 22, wherein said salt is a monosodium salt.

24. The method of claim 15, wherein said compound is applied to said wound in a pharmaceutically acceptable liquid carrier, wherein said compound is at a concentration of from about 200 µg/mL to about 500 µg/mL.

25. The method of claim 15, wherein said compound or a pharmaceutically acceptable salt thereof is applied to said wound in a plurality of administrations of said compound or salt.

26. The composition of claim 1, further comprising a sterile bandage including a wound healing-effective amount of said compound of the formula (I).

27. The composition of claim 2, further comprising a sterile bandage including a wound healing-effective amount of said compound of formula (I).

28. The composition of claim 3, further comprising a sterile bandage including a wound healing-effective amount of said compound of formula (I).

29. The composition of claim 25, further comprising a pre-packaged wound dressing comprising said sterile bandage including said compound of formula (I) or a pharmaceutically acceptable salt thereof, which bandage is sealed within a package.

30. The composition of claim 29, wherein said salt is a monosodium salt.

* * * * *